United States Patent [19]

Cooper

[11] Patent Number: 5,823,434
[45] Date of Patent: Oct. 20, 1998

[54] ELECTROMECHANICAL DRIVER FOR AN AEROSOL DISPENSING APPARATUS WHICH DISPENSES A MEDICATED VAPOR INTO THE LUNGS OF A PATIENT

[75] Inventor: Guy F. Cooper, Ventura, Calif.

[73] Assignee: The United States of America as represented by the Secretary of the Navy, Washington, D.C.

[21] Appl. No.: 841,817

[22] Filed: May 5, 1997

[51] Int. Cl.$^6$ ...................................................... B05B 1/08
[52] U.S. Cl. .................. 239/102.2; 239/398; 128/200.16; 128/203.12
[58] Field of Search ............................... 239/102.1, 102.2, 239/398; 128/200.14, 200.16, 203.12; 482/13

[56] References Cited

U.S. PATENT DOCUMENTS

| | | | |
|---|---|---|---|
| 4,667,877 | 5/1987 | Yao et al. | 239/102.2 |
| 5,361,989 | 11/1994 | Merchant et al. | 239/102.2 |
| 5,474,059 | 12/1995 | Cooper | 128/200.22 |
| 5,483,953 | 1/1996 | Cooper | 128/200.22 |

FOREIGN PATENT DOCUMENTS

| 4065 | 3/1992 | WIPO | 128/203.12 |
|---|---|---|---|

*Primary Examiner*—Andres Kashnikow
*Assistant Examiner*—Lisa Ann Douglas
*Attorney, Agent, or Firm*—David S. Kalmbaugh

[57] ABSTRACT

An aerosol dispensing apparatus comprises a housing which includes a top wall having a sharp edged orifice and a speaker assembly mounted on a bottom portion of the housing. A sawtooth waveform generator generates and then provides a sawtooth waveform signal which includes a jitter component to the speaker assembly which drives a flexible diaphragm resulting in a reciprocating motion of the flexible diaphragm. The ramp portion of sawtooth waveform signal retracts the flexible diaphragm in a rearward direction, while the approximately vertical portion of the signal causes an abrupt forward movement of the flexible diaphragm. The inner portion of the housing forms a chamber which contains a medication. The jitter component of the sawtooth waveform signal fluidizes the medication suspending the medication in air within the chamber to form a vaporized medication. Each cycle of the sawtooth waveform signal generates one ring vortex of a train of ring vortices with the ring vortex being generated during the vertical portion of the signal when the abrupt forward movement of the flexible diaphragm occurs.

5 Claims, 5 Drawing Sheets

ELECTROMECHANICAL DRIVER FOR AN AEROSOL DISPENSING APPARATUS WHICH DISPENSES A MEDICATED VAPOR INTO THE LUNGS OF A PATIENT

BACKGROUND OF THE INVENTION

1. Field of the Invention

The present invention relates generally to medical treatment apparatus. More specifically, the present invention relates to an electromechanical driver which may be used with a ring vortex aerosol projection apparatus for providing medication in a vapor form to the lungs of a patient having asthma or a like medical condition.

2. Description of the Prior Art

Patients suffering from asthma or any of the many other lung diseases require delivery of medication to the bronchial tubes and the alveolar air sachs in the lungs. At the present time there are three major ways of delivering aerosol treatment or medication to such patients, namely (1) nebulizers, which may be of the (a) venturi-jet type, or of the (b) ultrasonic piezoelectric type which produce aerosols from drug solutions; (2) metered dose inhalers (MDI) consisting of fluorocarbon or other gas pressurized canisters; and (3) dry powder inhalers (DPI) which may be (a) passive or (b) active. Dry powder inhalers also provide metered doses if sufficient suction is supplied by the patient.

Present day nebulizers for delivering medication to the lower recesses of the lungs are inefficient in that they deliver only 20 percent of the medicated aerosol beyond the trachea. The remainder of the vapor passes through the throat into the patient's stomach. This may result in serious side effects when a potent medication such as Pentamidine is being use to treat a patient lung disease. Increasing the dosage to compensate for the delivery inefficiency of the nebulizer may also be harmful to the patient.

While nebulizers can achieve the desired particle size of from 0.5 microns to 5.0 microns for the medication being delivered to the lungs, they are very inefficient in delivery of the medication to the lungs, especially the smallest bronchial tubes and alveolar air sachs of the lungs.

In addition, since a relatively small percentage of the medication reaches remote areas of the lung, the treatment may be ineffective, especially in smoke inhalation cases, pneumonia, or severe asthma attacks. In the case of smoke inhalation or severe asthma attacks, the medication which comprises generally anti-inflammatory drugs needs to reach the affected area of the lungs as quickly as possible to prevent permanent damage to the lungs and possible loss of life.

Metered dose inhalers which are both MDI and DPI have certain advantages over nebulizers because they are readily portable, and do not generally require an external power source such as compressed air or electricity. Metered dose inhalers are also capable of generating aerosols that are suitable for inhalation, more efficiently, reliably and cost effectively. The pressurized canister type of aerosol generator (MDI) includes a valve, which, when actuated, causes dispersement of a metered quantity of drug.

Because metered dose inhalers have previously used a chlorofluorocarbon as the propellant, and chlorofluorocarbons are believed to have a highly adverse effect on the ozone layer surrounding the earth, they are gradually being phased out to be replaced by the environmentally more friendly hydrofluorocarbons (e.g., HFC 134a and 227).

Such metered dose inhalers have become popular in that a droplet aerosol consisting of the drug particles and the fluorocarbon propellant is generated. The fluorocarbon propellant evaporates rapidly, and leaves smaller drug particles and clumps of particles, at least some of which are on the order of 1–3 microns aerodynamic mass median diameter which is the ideal size range for medication aerosols in humans. Unfortunately, many of the particles remain in larger clumps, and do not reach the necessary areas in the bronchi and lungs.

For example, some metered dose inhalers are relatively inefficient because they produce mainly non-respirable particles that range in size from about 35 micro-meters to about 1 micrometers. Of these particles only about 30 percent, chiefly particles under 5 micrometers, are actually capable of being inhaled. In practice this figure is closer to 20 percent. Most of the rest of the aerosol which is deposited in the throat has the potential for causing side effects, while not contributing to the therapeutic benefit.

There are some currently available powder inhalation systems which do not require a propellant. However, they do not function very effectively unless the patient can generate significant air flow rates, since it is the energy provided by the patient's forceful inhalation that not only mobilizes the powder but also breaks up the clumps thus preparing it for inhalation, in contrast with the high pressure of the fluorocarbon or other propellant in metered dose inhalers which accomplish the same end.

The patient's inhalation then carries the medication aerosol into the air passages via a mouthpiece. Current powder inhaler systems require strong inhalation on the part of the patient. They have not worked effectively with patients who cannot inhale vigorously.

In the metered dose inhalers noted above, it is common practice to include surfactants such as oleic acid. This presents problems. The fluorocarbon-medication suspension emerges as a liquid jet from the end of the valve stem or from the end of a cannula attached to the valve stem through which the metered dose inhaler contents have been forced and about 80 percent of it is deposited within three or four centimeters of the end of the valve or cannula. This results in an inefficient delivery system. It further has the disadvantage that large amounts of the surfactant material is deposited on the lining of the trachea, and the first few bronchi. It has been demonstrated that this causes injury to the airway lining with ulceration.

Over about the last 25 years systems for delivering medications to the lungs such as aerosol type delivery systems have become increasingly important for the treatment of airway diseases, particularly asthma and chronic obstructive pulmonary diseases, such as chronic bronchitis and emphysema as well as bronchiolitis and bronchiectasis. Other aerosol medications include mucolytic agents to thin secretions, the newest of which is deoxyribonuclease made by a recombinant method (rhDN-ase).

It is becoming increasingly important to deliver antibiotics directly to the airway for chronic illnesses such as cystic fibrosis, for treating a type of pneumonia in immunosuppressed patients (e.g., in AIDS), and for providing a new class of medications (sodium channel blockers) in cystic fibrosis to "lubricate" the secretions and make them easier to cough up or remove as a result of the action of cilia.

Aerosol systems for delivering medication directly to the patient's lungs generally fall into one of two categories, either (1) active or (2) passive. "Active" devices include (a) metered dose inhaler and (b) wet nebulizers. The pressurized canister metered dose inhaler generates the aerosol and directs it towards the patient independently of the patient's force of inhalation. This provides aerosol to the patient in a manner similar to so called "wet nebulizers" that aerosolize a drug solution. These "wet nebulizers" are jet nebulizers using the venturi principle, the energy source being compressed air which also serves to direct aerosol towards the spontaneously breathing or ventilation assisted patient, and ultrasonic nebulizers utilizing high speed vibration of a piezo-electric crystal and a blower fan to carry the medication aerosol to the patient. These are all active aerosol devices, since with the jet nebulizer it is the flow of oxygen or air through the device that creates the aerosol and drives it towards the patient who can then breathe in from a mouthpiece or mask. The ultrasonic nebulizer generates the aerosol into a space from which it can be inhaled by the patient breathing normally to inhale the mist with each inhalation, even if that inhalation is not vigorous. In addition, a blower can be incorporated which pushes the aerosol from the ultrasonic generator toward a mask or mouthpiece from which the patient inhales.

In contrast, currently available powder inhalers are "passive" devices in that the drug powder must reside in a small reservoir from which the patient can suck it by creating a relatively high inspiratory flow rate, usually over 30 liters per minute, and sometimes as high as 90–120 liters per minute if the optimum dose of medication is to be provided. This type of device has the advantage that aerosol is inhaled automatically when the patient inhales vigorously, but has certain disadvantages in that (a) there is considerable variability in dose depending upon how vigorously the patient inhales; (b) during severe episodes of asthma it may not be possible to create the high flow rates necessary to get a full dose of the drug which is particularly true of children under the age of 6; and (c) the greatest efficiency for aerosol inhalation is achieved at low inspiratory flow rates, 45 liters per minute and below, because at high flow rates small particles have greater inertia and therefore act like larger particles, thereby tending to be deposited in the back of the throat and around the larynx by impaction rather than being carried into the airways of the lungs where the medication must be deposited to be effective.

Another disadvantage of some widely prescribed current powder systems relates to exposure to the humidity of the environment of the drug reservoir where the fine particles are stored. Since many drug particles are very hygroscopic, repeated or continual exposure to humidity will greatly reduce the available dose due to swelling and clumping.

In view of the foregoing, what is needed is a relatively simple, yet highly effective aerosol dispensing apparatus which will effectively provide medication in a mist or vapor form to the bronchial tubes and the alveolar air sachs of the lungs of a patient without requiring the patient to inhale vigorously.

SUMMARY OF THE INVENTION

The present invention overcomes some of the disadvantages of the prior art including those mentioned above in that it comprises a relatively simple yet highly reliable and efficient dispensing apparatus which effectively provides medication in a mist or vapor form to the bronchial tubes and the alveolar air sachs of the lungs of a patient without requiring the patient to inhale vigorously.

In its simplest embodiment the dispensing apparatus comprises a housing which includes a top wall having a sharp edged orifice and a speaker assembly mounted on a bottom portion of the housing. The speaker assembly when energized drives a cone shaped flexible diaphragm of the speaker assembly with a reciprocating motion. Connected to the speaker assembly is a sawtooth waveform generator. The sawtooth waveform generator generates and then provides a sawtooth waveform signal which includes a jitter component to the speaker assembly driving the flexible diaphragm which results in the reciprocating motion of the flexible diaphragm. The ramp portion of sawtooth waveform signal retracts the flexible diaphragm in a rearward direction, while the approximately vertical portion of the signal causes an abrupt forward movement of the flexible diaphragm.

The inner portion of the housing forms a chamber which contains a medication which may be either in liquid form or powdered form. The jitter component of the sawtooth waveform signal fluidizes the medication within the chamber above the upper surface of the flexible diaphragm. Fluidizing the medication suspends the medication in air within the chamber to form a vaporized medication.

Each cycle of the sawtooth waveform signal generates one ring vortex of a train of ring vortices with the ring vortex being generated during the vertical portion of the signal when the abrupt forward movement of the flexible diaphragm occurs. During the ramp portion of the signal air from the atmosphere is drawn into chamber of the aerosol dispensing apparatus.

In another embodiment of the present invention, the aerosol dispensing apparatus may include multiple sharp edged orifices with each orifice having a counterflow ring positioned around the orifice.

DETAILED DESCRIPTION OF THE PREFERRED EMBODIMENTS

Figure 1:
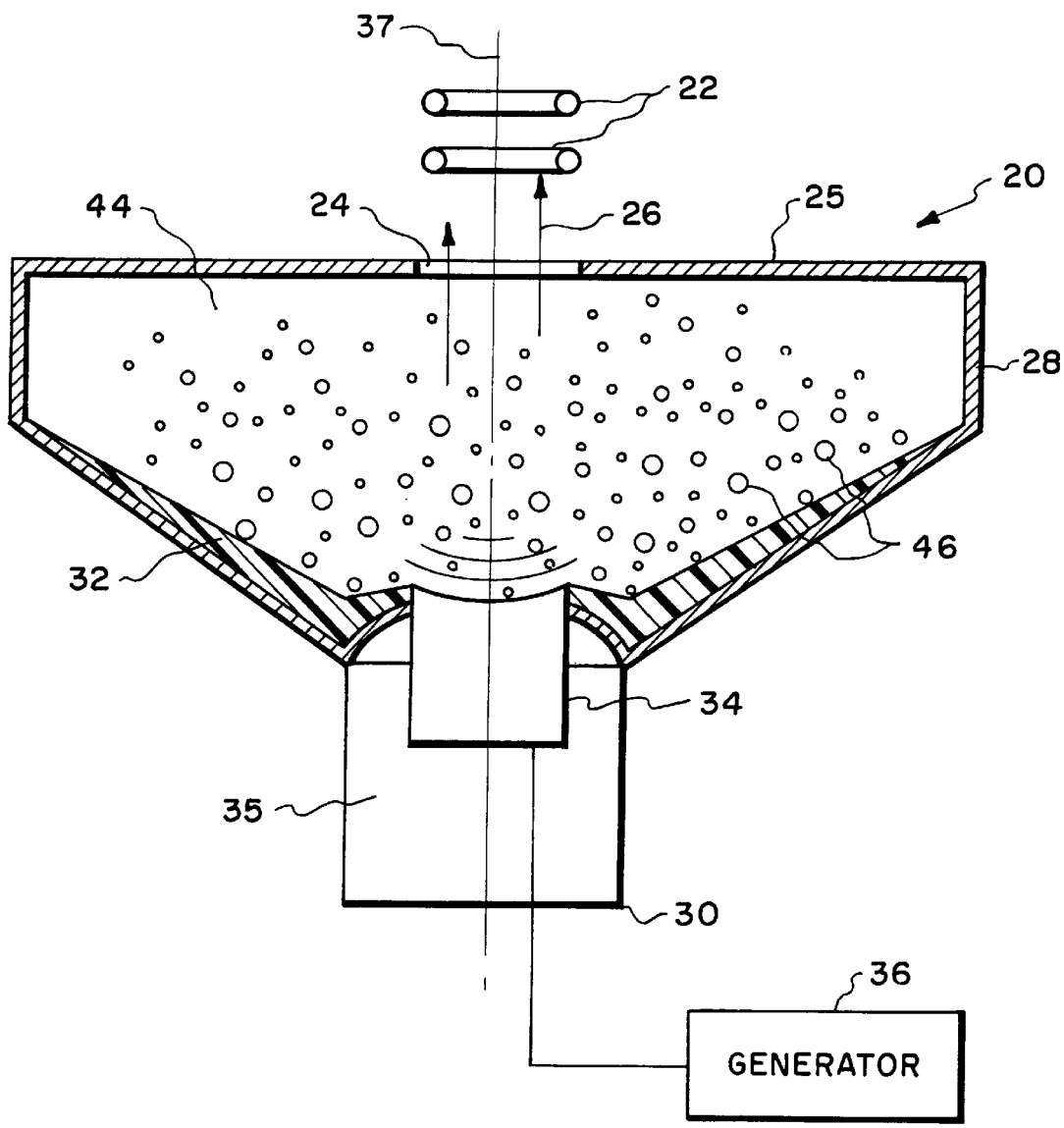
FIG. 1 is a simplified schematic diagram of an aerosol dispensing apparatus for dispensing a medicated mist which constitutes one embodiment of the present invention.
Figure 3:
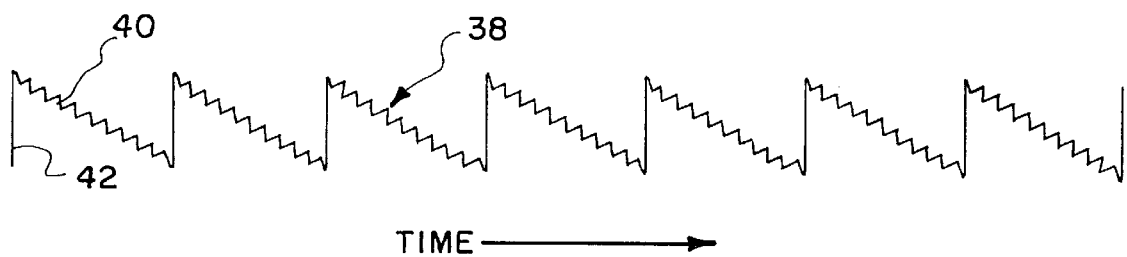
FIG. 3 illustrates the waveform used to drive solenoid of the aerosol dispensing apparatus of FIGS. 1 and 2.

Referring to FIGS. 1 and 3, there is shown an aerosol dispensing apparatus, designated generally by the reference numeral 20, for dispensing a medicated vapor or aerosol medication into the lungs of a patient having asthma or a like medical condition. Aerosol dispensing apparatus 20 generates a train of ring vortices 22 which exit dispensing apparatus 20 through a sharp edged orifice or opening 24 located at the top wall 25 of apparatus 20 in the manner indicated by arrow 26 prior to entering the lungs of a patient. The medicated vapor then enters the bronchial tubes and the alveolar air sachs of the patient's lungs treating the patient's medical condition.

Aerosol dispensing apparatus 20 comprises housing 28 which includes a top wall 25 and a speaker assembly 30 mounted on a bottom portion of housing 28. Speaker assembly 30 when energized drives a cone shaped flexible diaphragm 32 of the speaker assembly 30 with a reciprocating motion. Speaker assembly 30 also has a coil 34 which is coupled to flexible diaphragm 32 and a permanent magnet 35. Connected to the winding 34 of speaker assembly 30 is a sawtooth waveform generator 36. Generator 36, in turn, generates and then provides the sawtooth waveform signal 38 which includes a jitter component 40 to the winding 34 of speaker assembly 30 driving cone shaped flexible diaphragm 32 which results in the reciprocating motion of flexible diaphragm 32. The ramp portion of sawtooth waveform signal 38 retracts flexible diaphragm 32 in a rearward direction along the centerline axis 37 of aerosol dispensing apparatus 20. The steeply sloped approximately vertical portion 42 of signal 38 causes an abrupt forward movement of the flexible diaphragm 32 along the centerline axis 37 of apparatus 20. The sawtooth waveform signal 38 of FIG. 3 may have a frequency of up to 1000 hertz.

The inner portion of housing 28 forms a chamber 44 which has contained therein a medication which may be either in liquid form or powdered form. The jitter component 40 of the sawtooth waveform signal 38 fluidizes the medication within chamber 44 above the upper surface of diaphragm 32. Fluidizing the medication suspends the medication in air within chamber 44 to form an aerosol medication which is designated generally by the reference numeral 46.

Each cycle of the sawtooth waveform signal of FIG. 3 generates one ring vortex of the train of ring vortices 22 with the ring vortex being generated during vertical portion 42 of signal 38. During the ramp portion of the signal 38 air from the atmosphere is drawn into chamber 44 of aerosol dispensing apparatus 20.

Figure 2:
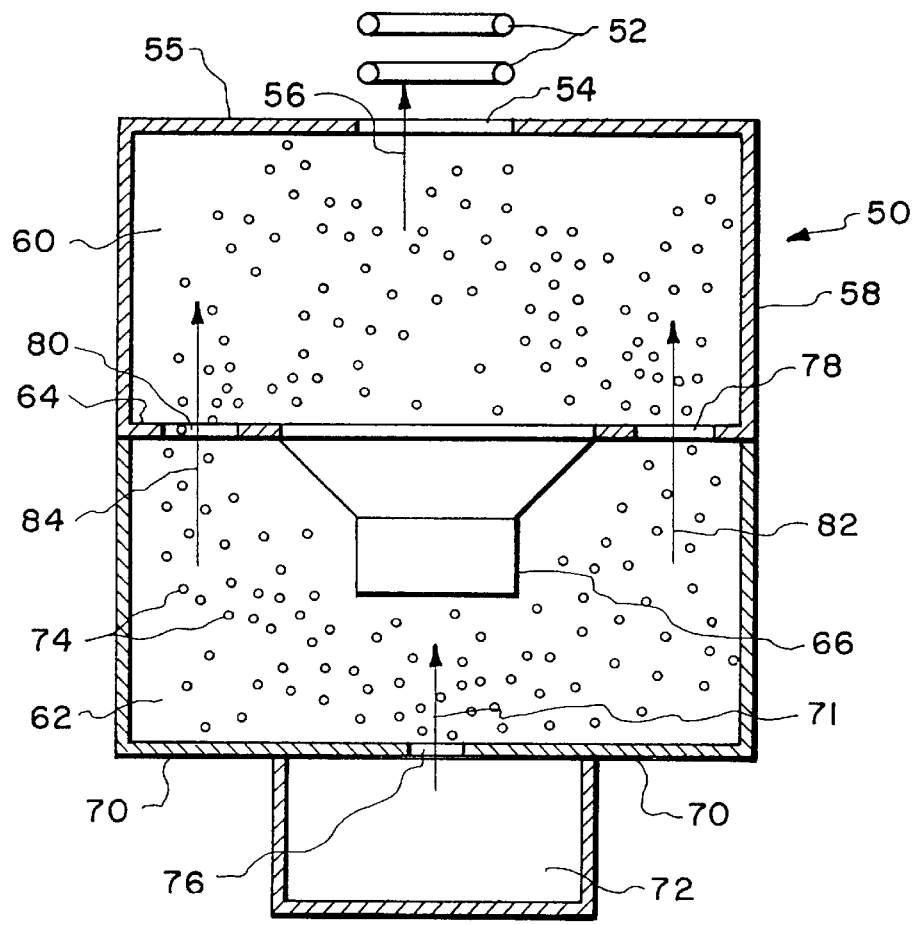
FIG. 2 is a simplified schematic diagram of another embodiment of the aerosol dispensing apparatus of the present invention.

Referring now to FIGS. 2 and 3, there is shown another embodiment of the aerosol dispensing apparatus which is designated generally by the reference numeral 50. Aerosol dispensing apparatus 50 also dispenses a medicated vapor or aerosol medication into the lungs of a patient having asthma or a like medical condition. Aerosol dispensing apparatus 50 generates a train of ring vortices 52 which exits dispensing apparatus 50 flowing through a sharp edged orifice or opening 54 located at the top wall 55 of apparatus 50 in the manner indicated by arrow 56 prior to entering the lungs of a patient. The medicated vapor then enters the bronchial tubes and the alveolar air sachs of the patient's lungs treating the patient's medical condition.

Aerosol dispensing apparatus 50 has a generally rectangular shape housing 58 which includes top wall 55. Housing 58 is partitioned into an upper chamber 60 and a lower chamber 62 by a speaker assembly support wall 64. Speaker assembly support wall 64, which is located approximately at the center point of housing 58, provides the support structure for a speaker assembly 66 which is identical to speaker assembly 30 of dispensing apparatus 20 of FIG. 1.

There is attached to the bottom of wall 70 of housing 58 a generally rectangular shaped aerosol generator 72 which provides medicated particles under pressure into lower chamber 62 through opening 76 within wall 70 as is best indicated by arrow 71. Lower chamber 62 of aerosol dispensing apparatus operates as a mixing chamber mixing medicated particles with air in lower chamber 62 resulting in a medicated vapor (indicated generally by the reference numeral 74).

After the mediated vapor 74 is formed in lower chamber 62. Medicated vapor 74 then flows through openings 78 and 80 within speaker assembly support wall 64 as indicated by arrows 82 and 84. The upper chamber 60 and speaker assembly 66 of aerosol dispensing apparatus 50 function in exactly the same manner as chamber 44 and speaker assembly 30 of the aerosol dispensing apparatus 50 of FIG. 1. Speaker assembly 66 is connected to a sawtooth waveform generator which generates and then provides the sawtooth waveform signal 38 (FIG. 3) including jitter component 40 to the winding of speaker assembly 66 to drive the cone shaped flexible diaphragm of speaker assembly 66 with a reciprocating motion. This reciprocating motion of the flexible diaphragm of speaker assembly 66 generates the train of ring vortices 52 which carries medicated vapor 74 to the patient's lungs.

Figure 4:
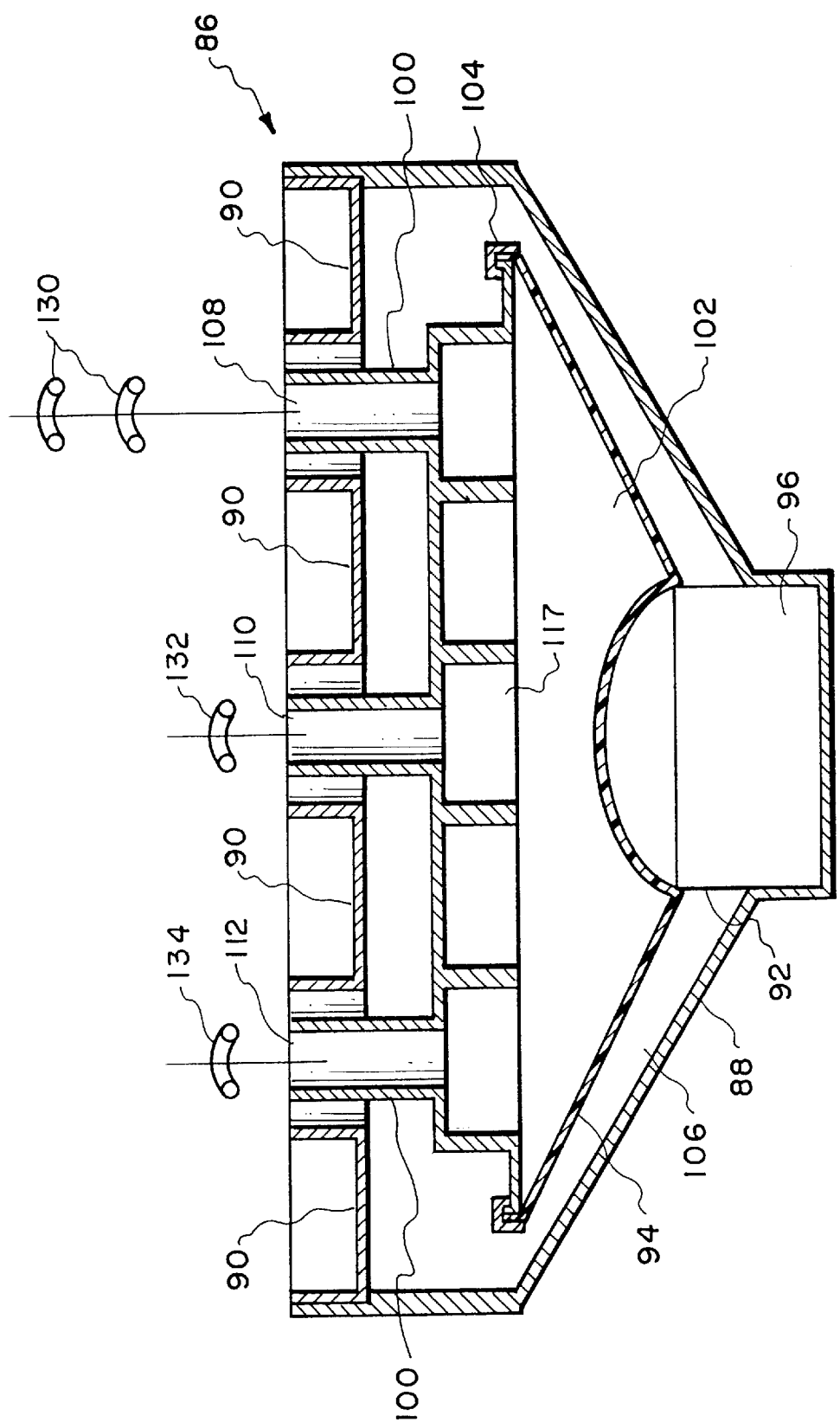
FIG. 4 is a schematic diagram of a multiple counter-flow orifice aerosol dispensing apparatus which constitutes a third embodiment of the present invention.
Figure 5:
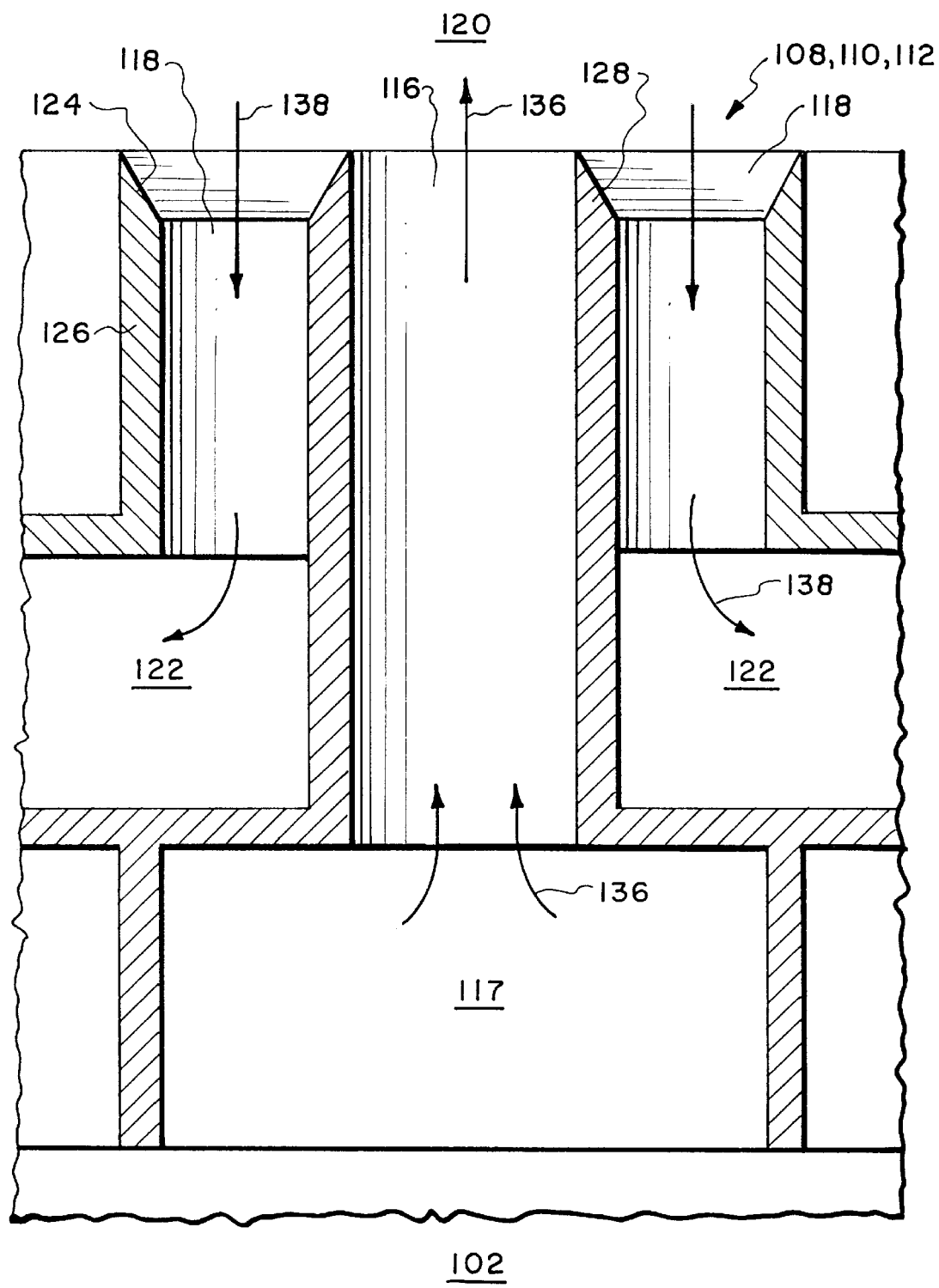
FIG. 5 is an enlarged view of one counter flow orifice of the aerosol dispensing apparatus of FIG. 4.

Referring now to FIGS. 3, 4 and 5, there is shown in FIG. 4 a third embodiment of an aerosol dispensing apparatus, designated generally by the reference numeral 86, for providing a medicated vapor or aerosol medication to the lungs of a patient having asthma or a like medical condition. Aerosol dispensing apparatus 86 comprises housing 88 which includes an orifice plate 90 extending across the top portion of housing 88 and a speaker assembly 92 mounted on a bottom portion of housing 88. Speaker assembly 92 when energized drives a cone shaped flexible diaphragm 94 of the speaker assembly 92 with a reciprocating motion. Speaker assembly 92 also has a coil (not illustrated) which is coupled to flexible diaphragm 94 and a permanent magnet 96.

Connected to the winding of speaker assembly 92 is a sawtooth waveform generator which is identical to the sawtooth waveform generator 36 illustrated in FIG. 1. The sawtooth waveform generator provides the sawtooth waveform signal 38 to the winding of speaker assembly 92 driving flexible diaphragm 94 which results in the reciprocating motion of flexible diaphragm 94.

The inner portion of housing 88 between the inner surface of flexible diaphragm 94 and an orifice support structure 100 of housing 88 forms a medication holding chamber 102. Medication holding chamber 102 has contained therein a medication which may be either in liquid form or powdered form. The orifice support structure 100 also has a diaphragm support rim 104 which attaches the cone shaped flexible diaphragm 94 to orifice support structure 100.

Housing 88 of aerosol dispensing apparatus 86 has therein a gaseous holding chamber 106 which is located generally between the outer surface of flexible diaphragm 94 and the inner surface of housing 88.

Orifice support structure 100 of aerosol dispensing apparatus 86 includes a plurality of counter flow orifices 108, 110 and 112 and is the support structure for the counter flow orifices 108, 110 and 112 of aerosol dispensing apparatus 86. FIG. 5 illustrates in detail each of the counter flow orifices 108, 110 and 112 of aerosol dispensing apparatus 86. It should be understood that the number of counter flow orifices of aerosol dispensing apparatus 86 may vary in accordance with the following: (1) the medication being dispensed by apparatus 86; (2) the desired ring vortex number, size and position geometry; and (3) the illness suffered by the patient being treated.

As is best illustrated in FIG. 5 each of the counter flow orifices 108, 110 and 112 of apparatus 86 comprises a cylindrical shaped orifice/opening 116 with an enlarged lower end portion 117 which operates as a plenum and an open concentric ring 118 positioned about the periphery of the upper end of orifice 116.

The upper end portion of orifice 116 communicates with the atmosphere 120, while the enlarged lower end portion 117 of orifice 116 is coupled to medication holding chamber 102 of housing 88. In a like manner, one end of concentric ring 118 communicates with the atmosphere 120, while the opposite end of ring 118 is coupled to air passageways 122 within orifice support structure 100. Air passageways 122 couple the concentric ring 118 of each of the counter flow orifices 108, 110 and 112 of apparatus 86 to gaseous holding chamber 106. This allows for air flow from the atmosphere 120 through the concentric rings 118 of counter flow orifices 108, 110 and 112 to gaseous holding chamber 106.

The top end 124 of the concentric ring 118 of each counter flow orifice 108, 110 and 112 is tapered or beveled to provide a sharp edge at the outer wall 126 of concentric ring 118 and the inner wall 128 of concentric ring 118 (as depicted in FIG. 5). The length of the tapered top end 124 of concentric ring 118 is about two and one half times the wall thickness of concentric ring 118.

Each cycle of the sawtooth waveform signal of FIG. 3 generates one ring vortex of the train of ring vortices 130, 132 and 134 respectively from counter flow orifices 108, 110 and 112. The ring vortex of each train of ring vortices 130, 132 and 134 is generated during the vertical portion 42 of signal 38. During the ramp portion of the signal 38 air from the atmosphere is drawn into medicated holding chamber 102 of aerosol dispensing apparatus 86.

Referring again to FIG. 5, it should be noted that each ring vortex is formed during vertical portion 42 of signal 38 (FIG. 3) by medicated vapor being expelled from chamber 102 through cylindrical shaped orifice 116 (as indicated by arrow 136) and the simultaneous drawing of air from the atmosphere 120 through concentric ring 118 (as indicated by arrow 138) into gaseous holding chamber 106.

Figure 6:
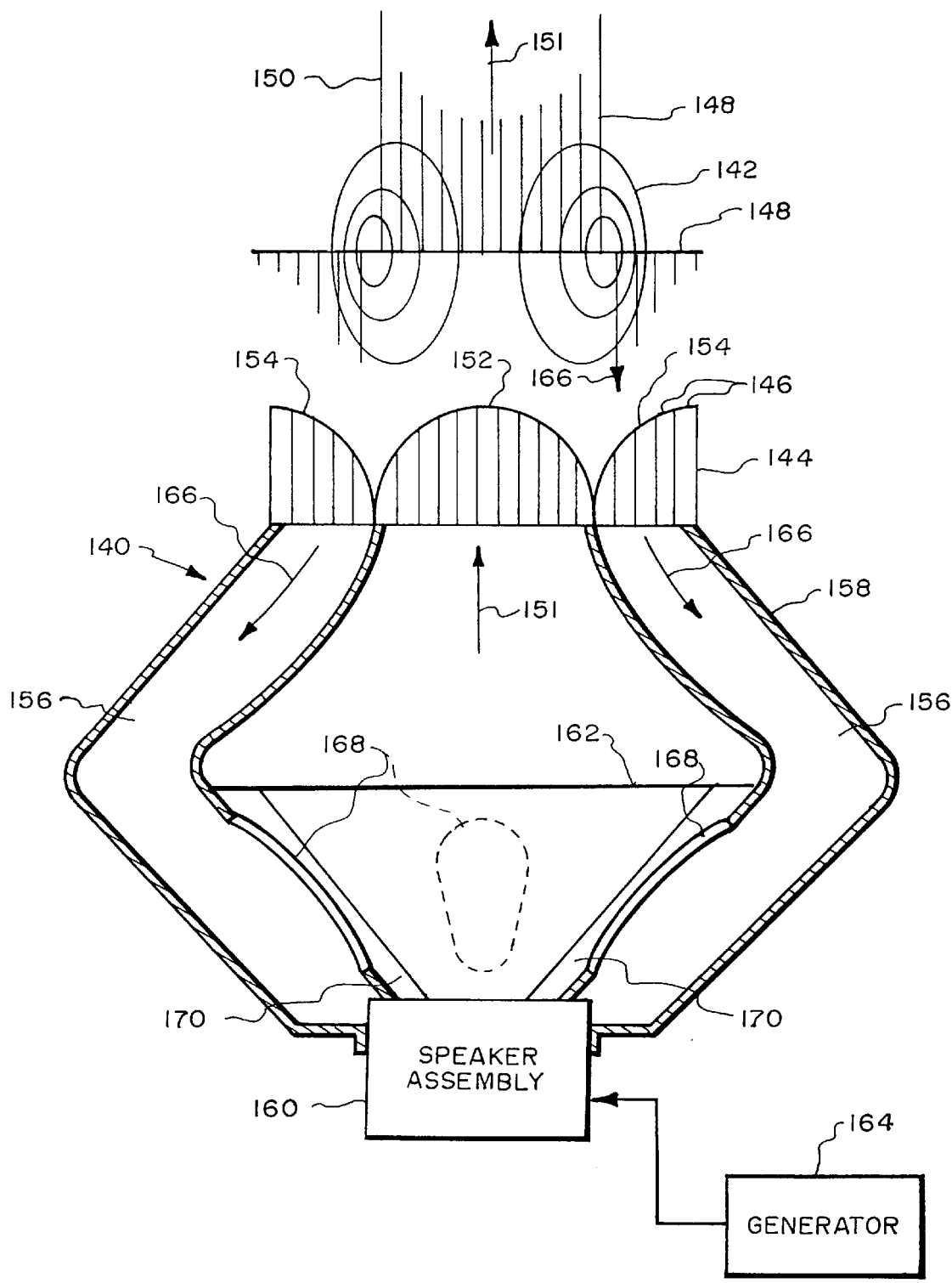
FIG. 6 is a schematic diagram of a single counter-flow orifice dispensing apparatus which constitutes a fourth embodiment of the present invention.

Referring to FIG. 6, there is shown an aerosol dispensing apparatus, designated generally by the reference numeral 140, for dispensing a medicated vapor into the lungs of a patient having asthma or a like medical condition. Aerosol dispensing apparatus 140 generates a ring vortex 142 which exits dispensing apparatus 140 through a contoured Hexcel or honeycomb flow structure 144 located at an upper portion of aerosol dispensing apparatus 140. The medicated vapor of ring vortex 142 then enters the bronchial tubes and the alveolar air sachs of the patient's lungs treating the patient's medical condition.

Contoured Hexcel structure 144 which comprises a plurality of elongated hexagonal shaped fluid passageways 146 of varying lengths shapes the air velocity profile 148 (by selective flow drag) to match the velocity profile 150 of the emerging ring vortex 142. The direction of propagation of the emerging ring vortex 142 is generally indicated by arrow 151.

As shown in FIG. 6, contoured Hexcel structure 144 is formed by a hemispherical shaped structure 152 and a quarter circle shaped structure 154 which is positioned about the perimeter of hemispherical shaped structure 152.

Aerosol dispensing apparatus 140 comprises housing 158 which has contoured Hexcel structure 144 affixed to a top portion thereof and a speaker assembly 160 affixed to housing 158 at a bottom portion thereof. Speaker assembly 160 when energized drives a cone shaped flexible diaphragm 162 of the speaker assembly 160 with a reciprocating motion. Connected to speaker assembly 160 is a sawtooth waveform generator 164. Generator 164, in turn, generates and then provides the sawtooth waveform signal 38 of FIG. 3 which includes a jitter component 40 to the speaker assembly 160 driving cone shaped flexible diaphragm 162 which results in the reciprocating motion of flexible diaphragm 162.

Housing 158 of aerosol dispensing apparatus 140 also has an air intake passageway 156 which is coupled to quarter circle shaped structure 154 allowing air from the atmosphere to be drawn into housing 158 via passageway 156 (as indicated by arrow 166). There is also located within housing 158 a plurality of vent holes 168 which allow for air flow from the atmosphere through passageway 156 to gaseous holding chamber 170 which surrounds the outer surface of flexible diaphragm 162.

At this time it should be noted that aerosol dispensing apparatus 140 may include a septum ring which is positioned between structure 152 and structure 154 of apparatus 140. The septum ring would be a thin cylindrical shaped structure having a height approximating the height of structure 152 and structure 154. The septum ring would separate the emerging ring vortex 142 flow (indicated by arrow 151) from counterflow air drawn into housing 158 via passageway 156 (indicated by arrow 166).

By utilizing elongated hexagonal shaped fluid passageways 146 of varying lengths, such as found in contoured Hexcel structure 144, a velocity profile of the type illustrated in FIG. 6 can be tailored for ring vortex 142. The following analysis illustrates the relationship of drag duct length of the passageways 146 of structure 144 to the desired velocity profile for ring vortex 142.

The first step is to calculate velocity head, $H_i$, of the air flow from any arbitrary passageway 146 of structure 144, which will be identified as the i-th passageway. The following passageway defines the relationship between velocity $V_i$ and velocity head $H_i$.

$$V_i = \sqrt{2gH_i} \qquad (1)$$

Velocity head loss $H_{DD}$ in the i-th passageway 146 is determined by the following equation.

$$H_{DD} = H_o - H_i \qquad (2)$$

where $H_o$ is the maximum velocity head generated by the motion of cone shaped flexible diaphragm 162 of speaker assembly 160.

The velocity head loss $H_{DD}$, resulting from flow through a passageway 146 of contoured Hexcel structure 144 is given by the Darcy-Weisbech equation:

$$H_{DD} = \frac{f}{4} \times \left(\frac{1}{R}\right) \times \frac{V^2}{2g} \qquad (3)$$

where:
  f=friction factor due to viscous and turbulent energy losses.
  (l/R)=the length, l, to hydraulic radius, R, ratio of the passageway 146.
  V=the velocity of air through the passageway 146 which is constant due to the assumed incompressibility of air and the constant cross section of the passageway.
  g=acceleration of gravity.

To determine the friction factor, f, the Reynolds number $N_{Re}$ (which is set forth in the following equation) must be determined.

$$N_{Re} = \frac{4VR\rho}{\mu} \qquad (4)$$

where:
  $\rho$=the density of air.
  $\mu$=the viscosity of air.

The friction factor, f, is a function of $N_{Re}$ according to the following equations. For $N_{Re} < 2000$ the following equation is used to determine f.

$$f = 4N_{Re} \quad (5)$$

For $N_{Re}=3000$ to $10,000$ the following equation is used to determine f.

$$\frac{1}{\sqrt{f}} = -2\log\left[\frac{e}{(14.8R)} + \frac{2.51}{(N_{Re}\sqrt{f})}\right] \quad (6)$$

where:
e=surface roughness of the inner surface of passageway.
log=log to base 10.

For $N_{Re}>10,000$ the following equation is used to determine f.

$$\frac{1}{\sqrt{f}} = 1.74 - 2\log\left(\frac{e}{2R}\right) \quad (7)$$

For smooth passageways, surface roughness may be neglected and the following equation may be used to determine f for $N_{Re}$.

$$\frac{1}{\sqrt{f}} = 2\log N_{Re}\sqrt{f} - 0.8 \quad (8)$$

The length l of the i-th passageway 146 is determined using equation (3) and the definition of the hydraulic radius, R, of a non-circular flow channel which is determined according to the following equation.

$$R = \frac{A_{x-sect}}{P_{wp}} \quad (9)$$

where the flow passage cross-section of a passageway 146 of the contoured Hexcel structure 144, $A_{x-sect}$, is given by:

$$A_{x-sect} = 1.5\sqrt{3} \times S^2 \quad (10)$$

and the wetted perimeter, $P_{wp}$ is given by:

$$P_{wp} = \frac{S}{\sqrt{3}} \quad (11)$$

where S is the length of a side of the passageway 146.

The initial velocity head provided by the speaker assembly 160 and flexible diaphragm 162 $H_o$ is diminished by the velocity head loss, $H_{DD}$, due to flow friction as air flows through the i-th passageway 146. From equations (1) and (2) the air velocity from the outlet end of the i-th passageway 146 is given by the following equation.

$$V_i = \sqrt{2g(H_o - H_{DD})} \quad (12)$$

The velocity profile of the ring vortex 142 may then be determined by the following equation which is the law of Biot-Savart. The law of Biot-Savart states that in a free vortex, the velocity about the vortex core filament varies inversely with the distance $r_i$.

$$V_i = \frac{k}{r_i} \quad (13)$$

where k is a constant having a magnitude which depends on the strength of the vortex.

To determine the passageway length at the center of the orifice, where $r_i = r_c$, the radius of the inner orifice, the velocity $V_i$ of equation (1) is set equal to a value appropriate to the free air propagation velocity of the departing ring vortex 142. From equation (1) $H_c$ is determined and used in equation (2) to determine $H_{DD}$ for the velocity head loss in the center passageway 146. The appropriate friction factor may be determined from equation 5, 6 or 7; the center passageway 146 length, l, may be calculated from equation (3). Equation (13) may now be used to calculate the value of the strength of the ring vortex K.

With the value of k available, the velocity at any radial distance from the edge of the inner orifice can be calculated, and with equations (1) and (2), velocity head loss $H_{DD}$ can be determined. In the same manner as for the center passageway, the length l for each passageway 146 of contoured Hexcel structure 144 can be calculated.

It should be noted from equation (2) that increasing velocities lead to decreasing velocity head loss $H_{DD}$ and thus decreasing passageway length, as shown in FIG. 6. It is therefore advisable to start near the periphery of structure 152 with a value of $r_i = \frac{1}{10} r_c$ and select a minimal length for the outer passageways 146.

From the foregoing, it may readily be seen that the present invention comprises a new, unique and exceedingly useful aerosol dispensing apparatus for effectively providing medication in a mist or vapor form to the lungs of a patient which constitutes a considerable improvement over the known prior art. Obviously many modifications and variations of the present invention are possible in light of the above teachings. It is therefore to be understood that within the scope of the appended claims, the invention may be practiced otherwise than as specifically described.

What is claimed is:

1. An aerosol dispensing apparatus comprising:
   a housing having a forward wall and an inner portion, the inner portion of said housing forming a chamber having a medication contained therein;
   a speaker assembly mounted on a bottom portion of said housing, said speaker assembly having a cone shaped flexible diaphragm;
   a signal generator connected to said speaker assembly, said signal generator providing a sawtooth waveform signal of a predetermined frequency to said speaker assembly, said sawtooth waveform signal having a ramp portion which includes a jitter component, the jitter component of said sawtooth waveform signal fluidizing said medication within said chamber to form an aerosol medication;
   said sawtooth waveform signal driving the cone shaped flexible diaphragm of said speaker assembly resulting in a reciprocating motion at said predetermined frequency for said cone shaped flexible diaphragm;
   said housing having an edged shaped orifice centrally located within the forward wall of said housing, said edged shaped orifice communicating with said chamber allowing said aerosol medication to exit said chamber and flow through said edged shaped orifice to form a ring vortex of aerosol medication;
   the reciprocating motion of said cone shaped flexible diaphragm at said predetermined frequency causing said aerosol dispensing apparatus to generate a train of said ring vortices of aerosol medication.

2. The aerosol dispensing apparatus of claim 1 wherein the predetermined frequency of said sawtooth waveform signal is between one hertz and one thousand hertz.

3. An aerosol dispensing apparatus comprising:
   a rectangular shaped housing having a front wall and a rear wall, said rear wall having a centrally located opening;
   an aerosol generator affixed to the rear wall of said rectangular shaped housing;
   a support wall centrally located within said rectangular shaped housing, said support wall partitioning said rectangular shaped housing to form a lower chamber and an upper chamber, said support wall having a plurality of openings;

said aerosol generator providing particles of a medication under pressure through the centrally located opening of said rear wall into said lower chamber, said lower chamber mixing the particles of said medication with air to form an aerosol medication, said aerosol medication flowing through the plurality of openings within said support wall into said upper chamber;

a speaker assembly mounted on said support wall, said speaker assembly having a cone shaped flexible diaphragm;

a signal generator connected to said speaker assembly, said signal generator providing a sawtooth waveform signal of a predetermined frequency to said speaker assembly, said sawtooth waveform signal driving the cone shaped flexible diaphragm of said speaker assembly resulting in a reciprocating motion at said predetermined frequency for said cone shaped flexible diaphragm;

said rectangular shaped housing having an edged shaped orifice centrally located within the front wall of said housing, said edged shaped orifice communicating with said upper chamber allowing said aerosol medication to exit said upper chamber and flow through said edged shaped orifice to form a ring vortex of aerosol medication;

the reciprocating motion of said cone shaped flexible diaphragm at said predetermined frequency causing said aerosol dispensing apparatus to generate a train of said ring vortices of aerosol medication.

4. The aerosol dispensing apparatus of claim 3 wherein the predetermined frequency of said sawtooth waveform signal is between one hertz and one thousand hertz.

5. The aerosol dispensing apparatus of claim 3 wherein said sawtooth waveform signal has a ramp portion which includes a jitter component.

\* \* \* \* \*